United States Patent [19]

Bellhouse et al.

[11] Patent Number: 6,004,286
[45] Date of Patent: Dec. 21, 1999

[54] PARTICLE DELIVERY

[75] Inventors: Brian John Bellhouse, Oxfordshire; Charles David Ogilvy Potter, Oxon; John Christopher Greenford, Oxfordshire, all of United Kingdom

[73] Assignee: PowderJect Research Limited, United Kingdom

[21] Appl. No.: 09/156,421

[22] Filed: Sep. 18, 1998

Related U.S. Application Data

[63] Continuation-in-part of application No. PCT/GB97/00734, Mar. 17, 1997.

[30] Foreign Application Priority Data

Mar. 19, 1996 [GB] United Kingdom .................. 9605690

[51] Int. Cl.[6] ...................................................... A61M 5/30
[52] U.S. Cl. ............................... 604/68; 604/58; 604/59; 604/69; 604/140
[58] Field of Search ................................. 604/68, 69, 70, 604/71, 72, 58, 59, 122, 131, 140, 141

[56] References Cited

U.S. PATENT DOCUMENTS

| | | |
|---|---|---|
| 5,630,796 | 5/1997 | Bellhouse et al. ...................... 604/500 |
| 5,836,911 | 11/1998 | Marzynski et al. ....................... 604/72 |
| 5,879,327 | 3/1999 | DeFarges et al. ......................... 604/68 |
| 5,899,880 | 5/1999 | Bellhouse et al. . |

FOREIGN PATENT DOCUMENTS

| | | |
|---|---|---|
| 96/04947 | 2/1996 | WIPO . |
| 96/12513 | 5/1996 | WIPO . |

*Primary Examiner*—Ronald Stright
*Assistant Examiner*—Jeremy Thissell
*Attorney, Agent, or Firm*—Thomas P. McCracken

[57] ABSTRACT

A needleless syringe, in which particles of a therapeutic agent are entrained in a high pressure gas flow, has a nozzle surrounded by a shroud silencer through which gas reflected from the target surface may be vented to atmosphere while retaining any particles reflected in the gas.

17 Claims, 3 Drawing Sheets

PARTICLE DELIVERY

CROSS REFERENCE TO RELATED APPLICATION

This application is a continuation-in-part of International Patent Application Number PCT/GB97/00734, filed Mar. 17 1997, designating the United States, from which priority is claimed pursuant to 35 U.S.C. §365(c) and which is incorporated herein by reference in its entirety.

TECHNICAL FIELD

The present invention relates generally to a needleless syringe for use in delivery of particles of a therapeutic agent to a target surface. More particularly, the invention is drawn to a needleless syringe system that is configured for delivery of particles of a therapeutic agent from a nozzle surrounded by a shroud that comprises a porous silencing material that allows discharged gas to vent to atmosphere but retains any particles reflected from the target surface within the confines of the shroud.

BACKGROUND OF THE INVENTION

In commonly owned U.S. Pat. No. 5,630,796, a noninvasive delivery system is described that entails the use of a needleless syringe device. The syringe is used for transdermal delivery of powdered therapeutic compounds and compositions to skin, muscle, blood or lymph. The syringe can also be used in conjunction with surgery to deliver therapeutics to organ surfaces, solid tumors and/or to surgical cavities (e.g., tumor beds or cavities after tumor resection).

The needleless syringe is constructed as an elongate tubular nozzle. Particles of a powdered therapeutic agent are located adjacent to the upstream end of the nozzle. The mechanics at the upstream end of the nozzle may involve a reservoir of gas such as helium, at a high pressure (e.g., between about 30 and 80 bar), and a high pressure gas flow is created by releasing the gas suddenly from the reservoir (e.g., by opening a valve), or by releasing the gas from the reservoir so that pressure builds up behind a membrane at the entrance to the nozzle until the membrane eventually ruptures to release the high speed gas flow. The particles may be contained initially within the high pressure gas reservoir or within a cassette from which the particles are released into the gas flow. The passageway through the nozzle itself is preferably convergent/divergent or convergent/cylindrical, with the upstream convergent section shorter than the downstream divergent or cylindrical section.

Since the gas pressure release from the above-described needleless syringe device is generally at or approaching supersonic speeds and can further involve the rupture of one or several membranes, the actual operation of the device can be quite noisy. In order to address this issue, the device was provided with a tubular shroud having a cylindrical silencer portion surrounding a downstream section of the nozzle. A spacer portion of the shroud extends axially beyond the exit plane of the nozzle to abut the target surface and positively space the exit plane of the nozzle from the target surface. An annular chamber was created between the nozzle and cylindrical silencer portion, wherein the chamber includes a series of baffles to create a tortuous path for escaping gas to pass through on its way through an upstream end of the silencer portion where several ports were provided for venting the gas to the atmosphere. Such a shroud is illustrated in FIGS. 1 to 3 of U.S. Pat. No. 5,630,796. Although practical for its intended purpose, such a shroud is still noisy owing to the comparatively large vent ports. In addition, it has been found that the tubular shroud configuration allows for particles reflected from the target surface to pass out of the ports even after multiple reflections from the series of baffles. Accordingly, there remains a need to provide a silencer mechanism that reduces the noise associated with operation of the needleless syringe and which contains any particles which may reflect from the target surface.

SUMMARY OF THE INVENTION

The present invention is particularly concerned with a novel and improved silencer mechanism provided at the downstream end of the nozzle of a needleless syringe device such as that described in U.S. Pat. No. 5,630,796. In this regard, it is desirable to dissipate and substantially silence both the sound pressure wave (noise) and gas flow which are discharged from the nozzle and which rebound from the target surface. This sound and pressure attenuation is effected by way of a judicious selection of device component configurations and silencing materials which together provide for the quiet and efficient operation of a needleless syringe. More particularly, the downstream construction of the device can provide for reactive attenuation of the sound and pressure (reflective attenuation structurally provided by a shroud or housing which surrounds the nozzle), dissipative attenuation of the sound and pressure (absorbent attenuation provided by a porous silencing material component of the shroud or housing, or attenuation provided by baffles), or a combination thereof. However, any system which includes a silencing element will have an inherent backpressure which is related to the amount of attenuation provided by the silencing element. Accordingly, the amount of reactive and/or dissipative attenuation provided by the present invention is carefully balanced in order to avoid creating an excessive increase in backpressure which could substantially affect the delivery performance of the device. Thus, the present attenuation mechanism readily allows for the external dissipation of the discharged gas pressure to avoid syringe recoil and lifting of the syringe away from the target. Furthermore, the attenuation mechanism is constructed so as to contain any and all of the small proportion of particles or particle fragments which may be reflected from the target surface, and thus prevents their uncontrolled release from the syringe.

It is thus a primary object of the invention to provide a silencing mechanism for use with a needleless syringe for delivering particles to a target surface. The syringe comprises an elongate nozzle having an upstream end and a downstream end. A means for releasing a high pressure flow of gas into the upstream end of the nozzle is provided, wherein particles entrained within the released gas flow pass through the nozzle and exit from the downstream end thereof for delivery to the target surface. In this regard, the nozzle is, or is arranged to be, connected at its upstream end to a source of high pressure gas. A source of particles of a powdered therapeutic agent is also provided at or adjacent to the upstream end of the nozzle. The particles can be disposed within a sealed cassette behind rupturable membranes, within a capsule, or contained within a high pressure gas reservoir. These particle retaining sources are described in U.S. Pat. No. 5,630,796, and in commonly owned International Patent Application Nos. PCT/GB95/01948, and PCT/GB95/02498, the disclosures of which are incorporated herein by reference. During operation of the needleless syringe, the gas flow is released by or through the particle source to entrain the particles.

The silencing mechanism is provided by a tubular shroud which surrounds the downstream end of the nozzle. The shroud has a downstream portion which extends beyond the downstream end of the nozzle and engages the target surface to establish a positive spacing between the nozzle and the target surface. The shroud further comprises a silencing material having a porous open structure. Both the sound pressure wave (noise) and gas flow which are discharged from the nozzle upon operation of the needleless syringe are initially contained by the tubular shroud, and must at some point pass through the silencing material. In this regard, the porosity of the silencing material is sufficient to allow escape of gas from the shroud while retaining any and all particles that may be reflected from the target surface.

The selection of a porous material having an appropriate porosity serves to actively contain within the shroud any and all particles or particle fragments which may have been reflected from the target, while at the same time allowing the discharged gas to pass out of the shroud through the material and thereby provide for a very effective silencing. This silencing (attenuation) feature may be enhanced by providing baffles within the shroud, for example by providing baffles within an annular chamber between at least a downstream section of the nozzle and a surrounding tubular portion of the shroud, or by providing steps on the outer surface of the nozzle and/or the inner surface of the shroud.

In particular aspects of the invention, the silencing material can be provided in the form of an inner or outer sleeve which is encompassed by, or surrounds a solid shroud housing having comparatively few large vents. Alternatively, an outer wall of the shroud can be formed partly or substantially completely of a substantially rigid porous silencing material.

In other aspects of the invention, an outer substantially rigid tubular wall of the shroud is provided with one or more gas exit openings, and the porous silencing material is a fibrous material, or a wadding of fibrous material which is used to close off a plurality of gas vents provided at an upstream end of the shroud.

It is also a primary object of the invention to provide a needleless syringe having a structural silencing mechanism. Here again, the syringe comprises an elongate nozzle having an upstream end and a downstream end. A means for releasing a high pressure flow of gas into the upstream end of the nozzle is provided, wherein particles entrained within the released gas flow pass through the nozzle and exit from the downstream end thereof for delivery to the target surface. The silencing mechanism is provided by a tubular shroud which surrounds the downstream end of the nozzle. The shroud has a downstream portion which extends beyond the downstream end of the nozzle and engages the target surface to establish a positive spacing between the nozzle and the target surface. The shroud is coaxially aligned with the nozzle and is spaced apart therefrom so as to establish an intermediate chamber between the outside of the nozzle and the inside of the shroud. The shroud further comprises a silencing structure which is in the form of a plurality of baffles which depend from the outside surface of the nozzle and/or from the inside surface of the shroud. The baffles can be arranged in a series to provide a tortuous path for escaping gas to pass through on its way from the nozzle to subsequent release from the shroud. Such baffles are sufficient to attenuate the gas flow and the attendant sound pressure wave. One or more gas vents are provided at an upstream portion of the shroud for venting the gas to atmosphere. A silencing material is provided somewhere within the path that the escaping gas must travel after discharge from the nozzle but prior to release through the gas vent(s).

In a particular aspect of the invention, an intervening tubular housing is provided which is also coaxially aligned with the nozzle. The intervening housing is disposed between the outside of the nozzle and the inside of the shroud in a spaced apart relation such that an inner intermediate chamber is established between the outside of the nozzle and the inside of the intervening housing, and an outer intermediate chamber is established between the outside of the intervening housing and the inside of the shroud. The intermediate chambers each comprise a plurality of depending baffles which attenuate the flow of gas discharged from the nozzle which then travels through the chambers for subsequent release from the shroud. If desired, the inner and outer intermediate chambers can communicate with each other only at their upstream portions such that gases discharged from the nozzle must travel through the inner chamber and then into the outer chamber for subsequent release from the shroud. Alternatively, the intervening housing can be comprised of a porous or perforated material which allows gas leakage between the inner and outer intermediate chamber substantially along their entire length.

Appropriate silencing materials for use in the present invention typically have a small pore size with a high void volume. The small pore size helps to maximize the particle filtering aspect of the invention, while the high void volume helps to minimize impedance of the gas flow (and thus minimize backpressure). Other physical characteristics which are taken into consideration in the selection of suitable silencing materials include the density, flow resistivity, and absorption coefficient associated with a particular material.

A suitable porous material for use as a silencing material in the shroud may be a sintered porous media, manufactured by dry powder moulding of particles of, for example, polyethylene (Porex®), polypropylene, a mixture of such sintered particles, or even of metal particles such as stainless steel or bronze. Other suitable porous materials for use with the invention include foams such as a polyurethane foam. If desired, the foam can be a reticulated polyurethane foam having a suitable compression density. In addition, fibrous materials can be employed, such as a wadding from a fibrous open pore material.

In addition, the silencing material may have more than one porosity, e.g., a coarse pore size inner layer and a fine pore size outer layer, or vice versa, or even a graded pore size from inside to outside. The finer material will catch any stray particles, whereas it is believed that the variable pore size will successively and more efficiently, attenuate and break up the sound pressure wave. In any regard, the porosity needs to be carefully chosen particularly in light of the range of particles sizes which are to be delivered from the needleless syringe. Too large a porosity will enable some stray particles to pass through the material to atmosphere. Too small a porosity or too thick a material will not readily allow the gas to pass through, thus causing a high pressure at the tip of the syringe which may result in unwanted recoil. Experiments with a drug having a mean particle size of 30 microns have successfully been carried out using a shroud made of an open pore solid material which has a mean pore size of 15 microns, a minimum pore size of 4 microns, and a porosity which is 55% solid and 45% void. The wall thickness was 3mm.

It is an advantage of the present invention that the noise associated with the operation of a needleless syringe device can be substantially attenuated without also reducing the delivery performance of the device. It is a further advantage that any and all particles or particle fragments reflected from the target surface can be contained within the device shroud and not vented to atmosphere.

These and other objects, aspects, embodiments and advantages of the present invention will readily occur to those of ordinary skill in the art in view of the disclosure herein.

BRIEF DESCRIPTION OF THE FIGURES

Examples of syringes constructed in accordance with the present invention are illustrated in the accompanying drawings, in which.

DETAILED DESCRIPTION OF THE PREFERRED EMBODIMENTS

Before describing the present invention in detail, it is to be understood that this invention is not limited to particular needleless syringe device configurations as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a," "an" and "the" include plural referents unless the content clearly dictates otherwise. Thus, for example, reference to "a silencing material" includes a mixture of two or more such materials, reference to "a baffle" includes two or more baffles, and the like.

A. Definitions

Unless defined otherwise, all technical and scientific terms used herein have the same meaning as commonly understood by one of ordinary skill in the art to which the invention pertains. The following terms are intended to be defined as indicated below.

The term "transdermal" delivery captures both transdermal (or "percutaneous") and transmucosal administration, i.e., delivery by passage of a therapeutic agent through the skin or mucosal tissue. See, e.g., *Transdermal Drug Delivery: Developmental Issues and Research Initiatives,* Hadgraft and Guy (eds.), Marcel Dekker, Inc., (1989); *Controlled Drug Delivery: Fundamentals and Applications,* Robinson and Lee (eds.), Marcel Dekker Inc., (1987); and *Transdermal Delivery of Drugs,* Vols. 1–3, Kydonieus and Berner (eds.), CRC Press, (1987). Aspects of the invention which are described herein in the context of "transdermal" delivery, unless otherwise specified, are meant to apply to both transdermal and transmucosal delivery. That is, the needleless syringe devices of the invention, unless explicitly stated otherwise, should be presumed to be equally useful in carrying out transdermal and transmucosal modes of delivery.

As used herein, the terms "therapeutic agent" and/or "particles of a therapeutic agent" intend any compound or composition of matter which, when administered to an organism (human or nonhuman animal) induces a desired pharmacologic, immunogenic, and/or physiologic effect by local and/or systemic action.

A "silencing material" encompasses any material which serves to reduce the intensity (magnitude) of a sound wave. A "sound wave" is defined herein to include any variation in atmospheric pressure that can be detected by the human ear. The normal human ear is responsive to a wide range of pressure variations (up to a factor of about $10^5$). A common measure of sound intensity is referred to in units of decibels (dB). Any sound wave that has an intensity in excess of 140 dB at any given time is considered excessive. The silencing materials used in the present invention may reduce (attenuate) the intensity of sound waves by any suitable mechanism, typically by way of their sound absorbing properties. Dissipative silencing absorbs sound by frictional loss in the silencing material, while reactive silencing reflects sound back towards the source. The silencing materials of the present invention can operate by dissipative or reactive silencing, a combination of dissipative and reactive silencing, or by any other suitable mechanism.

A "porous" material is any material that possesses or is full of pores (minute openings or interstices) which admit the absorption or passage of a fluid or sound wave. The "porosity" of a material is the ratio of the volume of interstices of a material to the volume of its mass.

B. General Methods

The needleless syringe device illustrated in FIG. 1 is similar in many respects to that illustrated in FIGS. 1 to 3 of U.S. Pat. No. 5,630,796. Thus the device has an upper barrel portion 10 providing a reservoir 11 of compressed gas, such as helium at between 30 and 80 bar. The upper barrel portion 10 is screwed or otherwise attached to a lower barrel portion 12 providing a rupture chamber 13. The lower barrel portion 12 is attached to the upper end of a nozzle 14 having a convergent/divergent passageway. Sealed between the lower barrel portion 12 and the upper end of the nozzle 14 is a cassette 15 comprising upper and lower rupturable membranes which retain a dose of a powdered therapeutic agent therebetween.

A lower or downstream portion 16 of the nozzle is surrounded by a shroud comprising a cylindrical portion 17 and a flared portion 18. The nozzle portion 16 has external annular ribs 19 that depend from the outer surface of the nozzle and interdigitate with internal annular ribs 20 depending from the inner surface of, or otherwise disposed within the shroud portion 17.

In use, the wider end 18 of the shroud is brought into contact with the target surface 21, typically a skin surface, and a knob 22 is depressed. This causes a valve stem 23 to move through the reservoir 11 so that a seal 24 moves out of an exit passageway of the reservoir and releases gas from the reservoir into the rupture chamber 13. As the pressure builds up, it eventually ruptures the membranes of the cassette 15, thereby releasing a high pressure gas flow through the nozzle with the particles of therapeutic agent entrained within the flow. These particles penetrate the target surface 21 to provide for the necessary transdermal delivery. The shroud portion 18 acts as a spacer which positively spaces the downstream end of the nozzle from the target surface and allows a degree of spread in the particles as they pass from the nozzle to the target. The shockwave (sound wave) resulting from the gas flow rebounds from the target surface, together with a small proportion of the particles, as suggested by the arrows 25, whereupon the pressure and noise of the shockwave are dissipated (attenuated) and any and all particles reflected from the target surface are caught within the shroud.

Figure 2A:
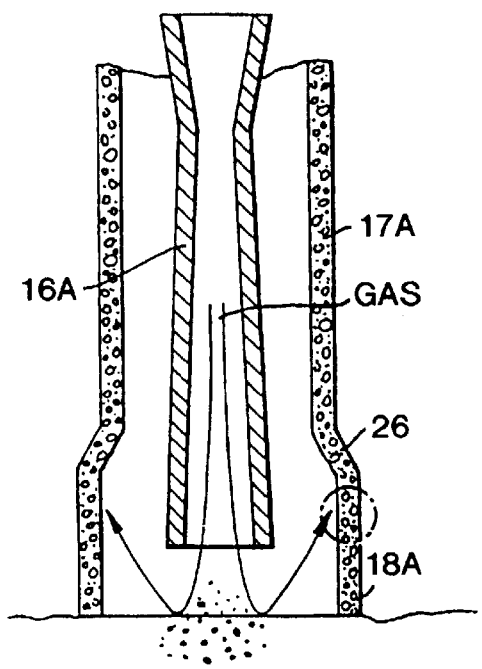
FIG. 2A is an axial section through the downstream end of another syringe embodiment.
Figure 2B:
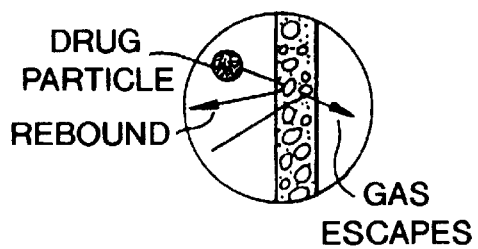
FIG. 2B is an enlargement of a section of FIG. 2A.

Dissipation of the sound wave caused by operation of the needleless syringe, and containment of the reflected particles can be achieved efficiently by constructing the shroud of an open pore material as shown in FIGS. 2A and 2B. FIG. 2. The shockwave is not only dissipated by having to traverse the tortuous path between the baffles formed by the interdigitating ribs 19 and 20, but also by passage through the porous outer wall of the shroud. Since at least the majority of the shroud is made up from such porous material, there is a minimum resistance to outflow of the gas through the shroud wall, thereby minimising any recoil of the syringe away from the patient's skin. However, the pore size is sufficiently small to retain any particles, or particle fragments, which may rebound from the target surface.

The shroud may be moulded in complementary halves, divided by an axial plane, so as to be fitted around the nozzle and between the ribs 19 upon assembly with the nozzle, prior to the halves being bonded together. The upper end of the shroud portion 17 can be bonded, snap fitted, or otherwise secured to the upper portion 14 of the nozzle by any suitable attachment means.

FIG. 2A shows a modification in which the baffles provided by the ribs 19 and 20 are omitted, but the shroud is provided with a step 26 between its smaller and larger diameter portions 17A and 18A surrounding the nozzle 16A. This step acts to some degree in providing adequate rebound surfaces to initiate dissipation of the shockwave and deceleration of any rebounding particles.

Figure 1:
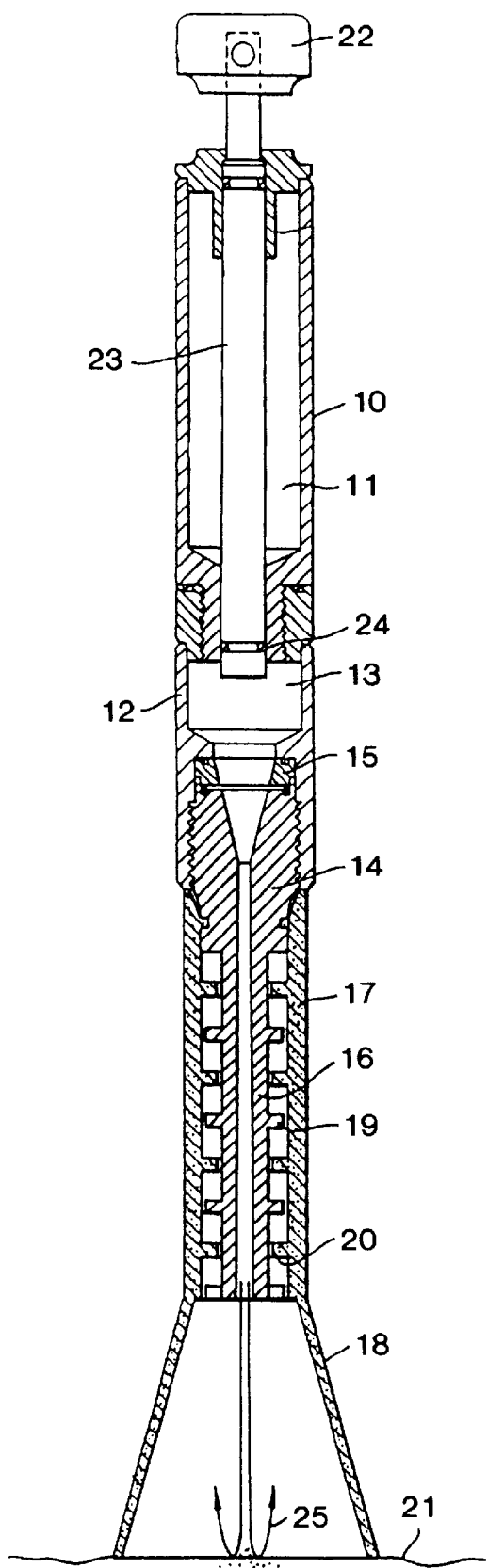
FIG. 1 is an axial section through a first syringe embodiment.
Figures 3, 4:
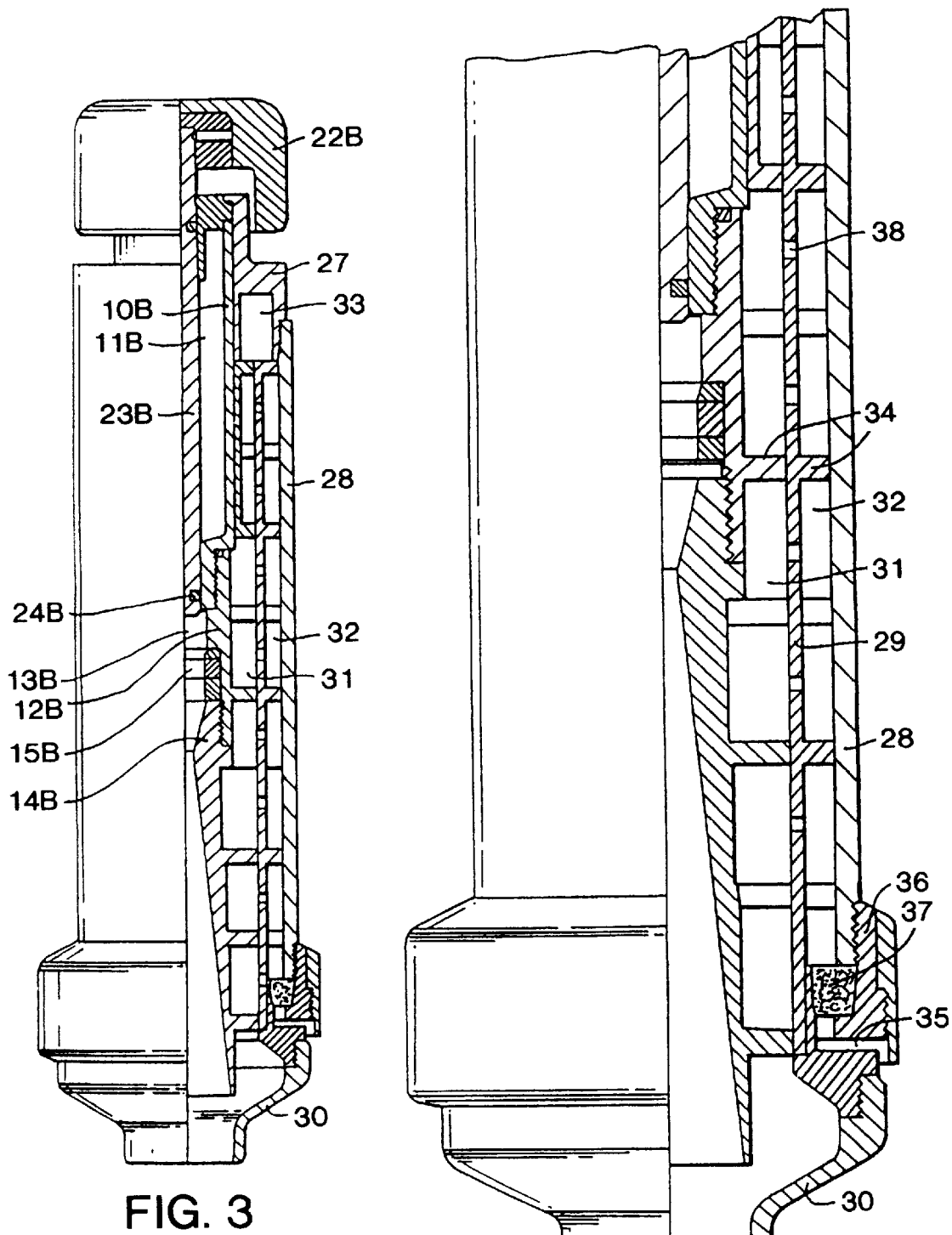
FIG. 3 is a half axial section of a third syringe embodiment.
FIG. 4 is an enlargement of a portion of the device of FIG. 4.

The needleless syringe device depicted in FIGS. 3 and 4 has a particle delivery mechanism which is similar to that of the device of FIG. 1. Components of the syringe device of FIGS. 3 and 4, which, although of a different detailed shape, have the same function as reference numerals 10–15 and 22–24 in FIG. 1, are given the reference numerals 10B–15B and 22B–24B. A repetitive description of these parts is therefore deemed unnecessary.

An essential difference between the needleless syringe of FIG. 3 and the syringe depicted in FIG. 1 resides in the construction and operation of the tubular shroud. More particularly, the tubular shroud in the device of FIG. 3 extends up almost to the top of the reservoir 11B and comprises a number of components which are welded, screwed, or otherwise attached together. These components include an upper portion 27, which is attached to the top of the upper barrel portion 10B, an outer cylindrical wall 28, an intervening cylindrical housing 29, and an outlet portion 30, into which the downstream end of the nozzle 14B opens. The outlet portion 30 is shown as having a generally frustoconical portion merging into a substantially cylindrical portion. This outlet section acts as a spacer which, when pressed against the target surface, positively spaces the downstream end of the nozzle a distance of about 10 mm away from the target surface.

The intervening tubular housing 29 divides the annular space between the inner surface of the shroud wall 28 and the outer surface of the nozzle 14B into two coaxial inner and outer intermediate chambers 31 and 32. These intermediate chambers are typically arranged in series, being interconnected at their top (upstream) ends by a hollow interior 33 of the upper portion 27 of the shroud. In addition, each intermediate chamber provides a tortuous path for a gas flowing therethrough by virtue of a plurality of discontinuous baffles 34. These baffles can depend from an outer surface of the nozzle 14B, a surface of the intervening housing 29, and/or from an inner surface of the outer cylindrical wall 28 of the shroud. In each intermediate chamber (31 and 32), these baffles can be axially spaced about 10 mm apart and consists of an annular disc with two diametrically opposed slots, each occupying about 60° of arc, with the slots in one baffle 90° out of alignment with those in the adjacent baffle in the same chamber. As can be seen in FIGS. 3 and 4, the lower end of the inner intermediate chamber 31 is open to the interior of the outlet portion 30. The lower end of the outer intermediate chamber 32 communicates with a ring of gas vent exit openings 35, disposed within a nut member 36, wherein each opening is provided by a bore having a diameter of about 2 mm. Located between the shroud wall 28 and the nut member 36 is an annular ring of cotton-wool wadding 37 which isolates the interior of the chamber 32 from the openings 35.

In use, the flow of gas discharged from the nozzle, and any particles reflected from the target surface, are caused to pass up through the inner intermediate chamber 31, following a tortuous path around the baffles 34, travel through into the upstream end of the outer intermediate chamber 32 (via the hollow interior portion 33 of the upper shroud portion 27), whereafter the gas and possibly some of the reflected particles pass down again along a tortuous path around the baffles 34. The gas is then able to permeate through the wadding 37 and hence be vented to atmosphere through the openings 35 while the wadding 37 captures any residual particles.

The larger the volume of the intermediate chambers 31 and 32 the better. However, it has been found in practice that a vented volume of about 80 ml works very well.

The function of the silencer mechanism of FIGS. 3 and 4 can be enhanced if there is provision for leakage of gas from the inner intermediate chamber 31 to the outer intermediate chamber 32 through the intervening tubular housing 29. This may be provided for by forming a portion of the housing 29 from a porous silencing material, or by including perforations 38 in the housing. One particular embodiment of the invention uses an arrangement of four equalangularly spaced holes through the housing 29 between each pair of baffles 34. Those holes which are physically further away from the target surface (upstream, i.e., higher up in FIGS. 3 and 4), are preferably a little larger than those lower down. For example, holes in the upper half may be 2 mm in diameter and those in the lower half 1.5 mm in diameter. As an alternative to the holes 38, the intervening tubular housing 29 can be comprised substantially of an open pore silencing material.

Experiments show that the construction shown in FIGS. 3 and 4 enables the noise level to be reduced to an acceptable level of below 80 dB at 1 m distance with an applied load of 20 N.

The syringe of FIG. 5 has a particle delivery mechanism similar to those of the devices described herein above, and repetitive description of these features is thus deemed unnecessary. Here again, substantially identical components are numbered alike. In the instant syringe, yet another construction and operation of the shroud is used to silence the operation of the device.

Figure 5:
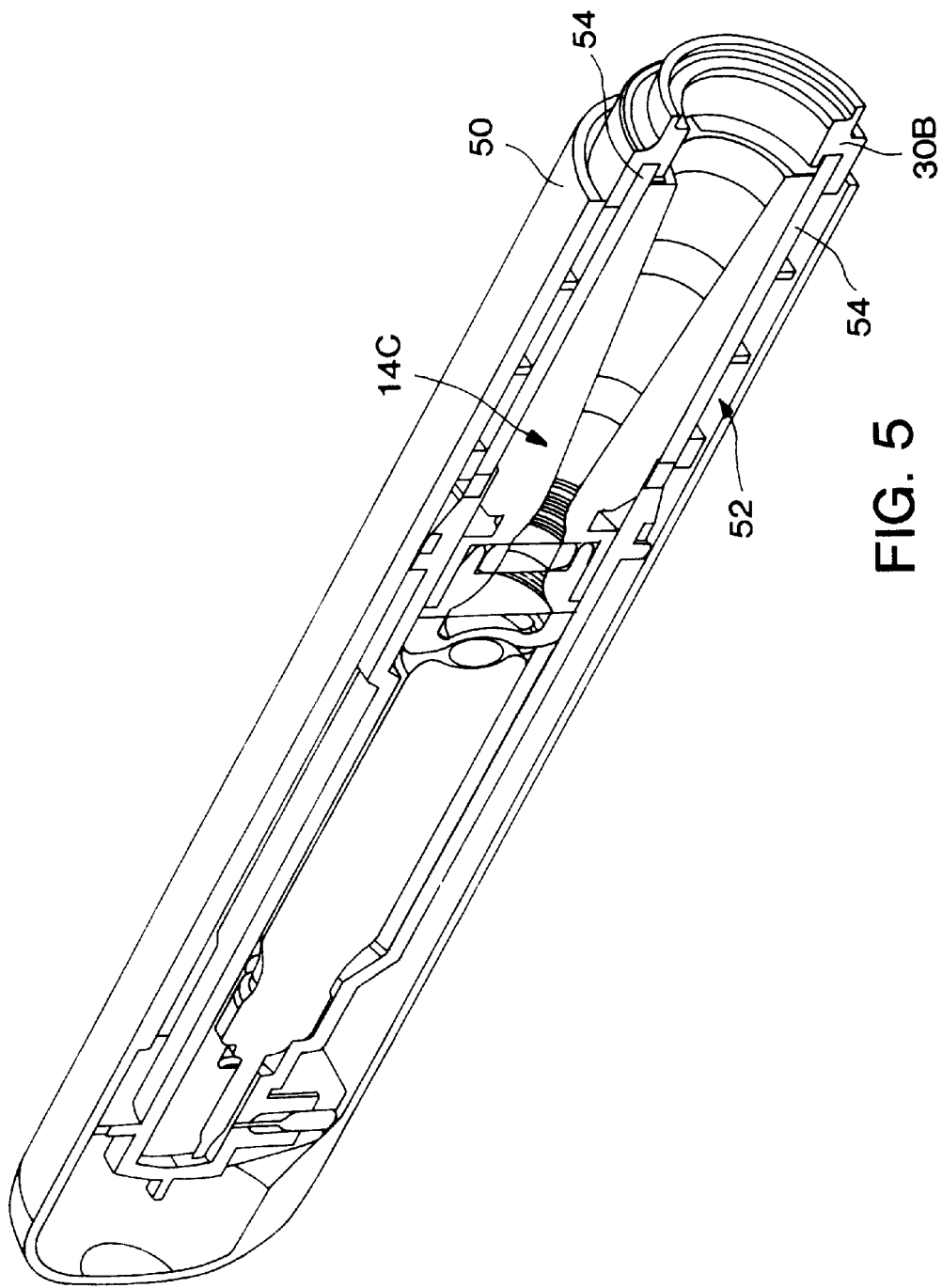
FIG. 5 is an axial section of a fourth syringe embodiment.

Referring particularly to FIG. 5, the shroud comprises a number of components which are welded, screwed, or otherwise attached together. These components include a substantially rigid outer wall 50 having a plurality of gas exit openings 52 disposed therein. A silencing material 54 is disposed between an inner surface of the outer wall 50 and an outer surface of the nozzle 14C. An outlet portion 30B, into which the downstream end of the nozzle 14C opens acts as a spacer which, when pressed against the target surface, positively spaces the downstream end of the nozzle a distance of about 10 mm away from the target surface. The silencing material 54 is comprised of a suitable open pore material, preferably from a sheet of reticulated polyurethane foam.

In use, the flow of gas discharged from the nozzle, and any particles reflected from the target surface, must pass up through the silencing material 54, whereupon the gas is able to permeate through the silencing material 54 and hence be vented to atmosphere through the openings 52, while the silencing material 54 prevents escape of any reflected particles.

Accordingly, novel silenced needleless syringe device are disclosed. Although preferred embodiments of the subject invention have been described in some detail, it is understood that obvious variations can be made without departing from the spirit and the scope of the invention as defined by the appended claims.

We claim:

1. A needleless syringe for delivering particles to a target surface, said syringe comprising:

(a) an elongate nozzle having an upstream end and a downstream end;

(b) means for releasing a high pressure flow of gas into the upstream end of the nozzle, wherein particles entrained within the released gas flow pass through the nozzle and exit from the downstream end thereof for delivery to the target surface; and (c) a tubular shroud surrounding the downstream end of the nozzle, wherein said shroud has a downstream portion which extends beyond the downstream end of the nozzle and engages the target surface, and further wherein said shroud comprises a silencing material having a porous open structure the porosity of which is sufficient to allow escape of gas from the shroud while retaining any particles reflected from the target surface.

2. The syringe of claim 1, wherein the shroud is coaxially aligned with the nozzle and spaced apart from the nozzle to provide an intermediate chamber between the outside of the nozzle and the inside of the shroud, said intermediate chamber comprising a plurality of baffles depending from the outside of the nozzle or the inside of the shroud, wherein said baffles are sufficient to attenuate the flow of gas discharged from the nozzle which passes through the intermediate chamber for subsequent release from the shroud.

3. The syringe of claim 2 further comprising an intervening tubular housing which is coaxially aligned with the nozzle and disposed between the outside of the nozzle and the inside of the shroud, said intervening housing being spaced apart from the nozzle and the shroud to establish inner and outer intermediate chambers, wherein said intermediate chambers have a plurality of depending baffles which are sufficient to attenuate the flow of gas discharged from the nozzle which passes through the inner and outer intermediate chambers for subsequent release from the shroud.

4. The syringe of claim 3, wherein the intervening tubular housing is porous or perforated to allow gas leakage between the inner and outer intermediate chambers.

5. The syringe of claim 4, wherein the intervening tubular housing is formed from an open pore foam.

6. The syringe of claim 3, wherein the inner and outer intermediate chambers are in fluid communication with each other only at upstream portions thereof such that gas discharged from the nozzle must pass through the inner chamber and then into the outer chamber for subsequent release from the shroud.

7. The syringe of claim 1, wherein the silencing material has a small pore size and a high void volume.

8. The syringe of claim 7, wherein the silencing material is a foam.

9. The syringe of claim 8, wherein the silencing material is a polyurethane foam.

10. The syringe of claim 1, wherein the shroud comprises a substantially rigid outer wall having one or more gas exit openings, and the silencing material is comprised of an open pore material disposed between the outer wall and the nozzle.

11. The syringe of claim 10, wherein the silencing material is comprised of an open pore foam which substantially surrounds the downstream end of the nozzle and is sandwiched between the nozzle and the outer wall of the shroud.

12. The syringe of claim 11, wherein the silencing material is a polyurethane foam.

13. The syringe of claim 1, wherein the shroud comprises a substantially rigid outer wall having one or more gas exit openings, and the silencing material is comprised of a fibrous open pore material disposed within or closing said one or more gas exit openings.

14. The syringe of claim 13; wherein the silencing material is a wadding of fibrous open pore material.

15. The syringe of claim 1, wherein the silencing material is a substantially rigid open pore material.

16. The syringe of claim 1, wherein the silencing material has a fibrous structure.

17. The syringe of claim 1, wherein the shroud comprises an inner or outer wall which is substantially comprised of the silencing material.

* * * * *